United States Patent [19]

Sakimae et al.

[11] Patent Number: 5,476,791

[45] Date of Patent: Dec. 19, 1995

[54] PROCESS FOR PRODUCING OPTICALLY ACTIVE CARBOXYLIC ACID AMIDE

[75] Inventors: Akihiro Sakimae, Ohtake; Yuri Kagawa, Hiroshima; Ryozo Numazawa, Ohtake; Hisao Onishi, Hiroshima, all of Japan

[73] Assignee: Mitsubishi Rayon Company, Limited, Tokyo, Japan

[21] Appl. No.: 243,521

[22] Filed: May 16, 1994

Related U.S. Application Data

[63] Continuation of Ser. No. 869,132, Apr. 15, 1992, which is a continuation-in-part of Ser. No. 821,142, Jan. 16, 1992, which is a continuation-in-part of Ser. No. 737,488, May 24, 1985, abandoned.

[30] Foreign Application Priority Data

Aug. 16, 1984 [JP] Japan ................... 59-169932

[51] Int. Cl.$^6$ .................................................. C12P 9/00
[52] U.S. Cl. ................ 435/280; 435/131; 435/170; 435/822
[58] Field of Search ................... 435/280, 131, 435/170, 822

[56] References Cited

U.S. PATENT DOCUMENTS

| | | |
|---|---|---|
| 4,154,935 | 5/1979 | Oudehi ........................ 548/533 |
| 4,415,657 | 11/1983 | Umezawa et al. . |
| 4,584,270 | 4/1986 | Sih . |

FOREIGN PATENT DOCUMENTS

| | | |
|---|---|---|
| 0008831 | 3/1980 | European Pat. Off. . |
| 55-118456 | 9/1980 | Japan . |
| 7094295 | 6/1982 | Japan . |

OTHER PUBLICATIONS

Goodfellow et al, "The Biology of the Actinomycetes", pp. 92–93, 1984, Academic Press, The ATCE Catalogue of Yeasts, 1990, p. 9.

*Primary Examiner*—Irene Marx
*Attorney, Agent, or Firm*—Oblon, Spivak, McClelland, Maier & Neustadt

[57] ABSTRACT

N-(3-acetylthio-2-D-methylpropionyl)-L-proline useful as a precursor of captopril, one of antihypertensive agents, is prepared by allowing thioacetic acid to react with methyl methacrylate to prepare racetalc methyl 3-acetylthio-2-DL-methylpropionate, contacting the propionate with cells of, for example, Pseudomonas in order to effect biological and asymmetric hydrolysis, extracting 3-acetylthio-D-2-methylpropionic acid and allowing the acid to react with L-proline.

2 Claims, No Drawings

PROCESS FOR PRODUCING OPTICALLY ACTIVE CARBOXYLIC ACID AMIDE

This application is a Continuation of application Ser. No. 07/869,132, filed on Apr. 15, 1992, which is a CIP of 07/821,142 filed Jan. 16, 1992 which is a CIP of 06/737,488 filed May 24, 1985, now abandoned.

The present invention relates to a novel process for producing optically active carboxylic acid amides of he formula (I);

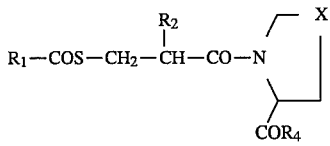 (I)

wherein $R_1$ is an alkyl group, an aralkyl group or an aryl group, $R_2$ is an alkyl group, $R_4$ is a hydroxyl group, an amino group or an alkoxy group, and X is a hydrogen, a methylene group or a sulfur atom.

The present invention specifically relates to a novel process for producing an optically active carboxylic acid amide, N-(3-acetylthio-2-D-methylpropionyl)-L-proline, of the formula (II);

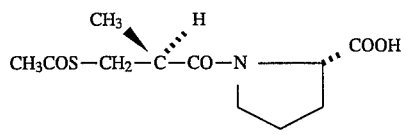 (II)

The optically active carboxylic acid amides of the formula (I) have varieties of physiological activities and are useful as a medicinal agent, particularly as an antihypertension agent. N-(3-acetylthio-2-D-methylpropionyl)-L-proline of the formula (II) is a precursor of captopril, one of antihypertensive agents. It is important that 3-acetylthio-2-methylpropionyl portion is a D-form.

Ondetti et al (U.S. Pat. No. 4,154,935) discloses a process wherein thioacetic acid is allowed to react with methacrylic acid to obtain racemic 3-acetylthio-2-D,L-methylpropionic acid, the acid is further allowed to react with L-proline to obtain a diastereomer mixture of N-(3-acetylthio-2-D,L-methylpropionyl)-L-proline, and the mixture is physically and optically hydrolyzed to obtain N-(3-acetylthio-2-D-methyl-propionyl)-L-proline. The hydrolysis adove requires complicated operations and yield is so small that the process is not economical. All we can do is to waste another moiety of diastereomer by-produced, since the diastereomer has two asymmetric carbons and racemization is hardly effected.

There is a biochemical and asymmetrical hydrolysis of racetalc carboxylic acid esters to obtain optically active carboxylic acids. However, a specific esterase rarely works to all compounds having ester groups. Umezawa et al (U.S. Pat. No. 4,415,657) teach a hydrolysis reaction of

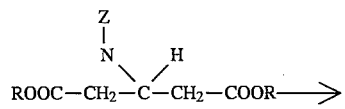

-continued

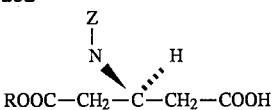

by use of 36 microorganisms such as Arthrobacter, Corynebacterium etc. Sih (U.S. Pat. No. 4,584,270) teaches a hydrolysis of

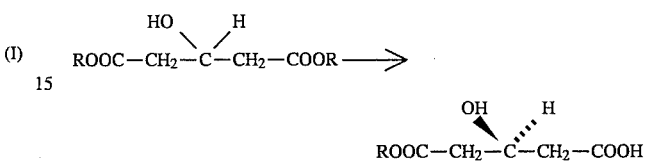

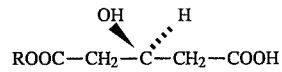

by use of six microorganisms such as Arthrobacter, Corynebacterium etc. However, these microorganisms do not work in the present reaction.

Hitherto, as a process for producing the optically active carboxylic acid amides mentioned above, a process is known wherein physicochemical resolution of racemic carboxylic acids, such as 3-thiobenzoyl-2-alkylpropionic acid, with an optical resolving agent is effected to produce optically active carboxylic acids, and then the acids are allowed to react with amine derivatives, such as proline (EP-8831 and WPI 80-76079c/43 ).

However, this process is not satisfactory yet froin an economical point of view, since there are drawbacks in that a large amount of an expensive resolving agent is needed in the steps of the resolution for preparing optically active carboxylic acids, that the resolution is very complicated, and that a small amount of the resolving agent is liable to be left unremoved as an impurity in the product. Appearance of more expedient and economical process without such drawbacks has been desired for producing optically active carboxylic acids.

After having extensively studied processes for producing optically active carboxylic acids requiring no such resolving agents and processes for producing optically active carboxylic acid amides from the produced optically active carboxylic acid obtained above, the present inventors have succeeded in finding that optically active carboxylic acids are easily prepared by use of enzymes or microorganisms, and that the optically active carboxylic acid amides are obtainable by allowing the optically active carboxylic acid to react with amine compounds.

The present invention provides a process for producing optically active carboxylic acid amides of the formula;

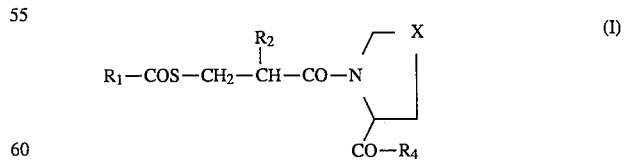 (I)

wherein $R_1$, $R_2$, $R_4$ and X are as defined above, which comprises allowing carbothioic acids of the formula;

 (III)

wherein $R_1$ is as defined above, to react with unsaturated carboxylic acid esters of the formula;

wherein $R_2$ and $R_3$ each represents an alkyl group, to obtain esters of the formula;

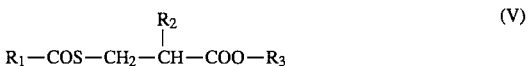

wherein $R_1$, $R_2$ and $R_3$ are as defined above, biochemically and asymmetrically hydrolyzing the esters of the formula (V) above to obtain optically active carboxyLic acids of the formula;

wherein $R_1$ and $R_2$ are as defined above and * represents an optically active carbon, and allowing the optically active carboxylic acids of the formula (VI) above to react with amine compounds of the formula;

wherein $R_4$ and X are as defined above.

As for the substituent $R_1$, there may be exemplified methyl, ethyl and propyl groups for an alkyl group, benzyl group for an aralkyl group and phenyl group for an aryl group. The alkyl group for the substituents $R_2$ and $R_3$ may be, for example, methyl group or ethyl group.

In practicing the process of the present invention, the esters of the formula (V) above are prepared first by allowing the carbothioic acid of the formula (III) to react with the unsaturated carboxylic acids of the formula (IV). It is preferable to carry out this reaction step in the presence of a polymerization inhibitor, such as hydroquinone, in order to inhibit the unsaturated carboxylic acids of the formula (IV) from polymerization thereof. This reaction may be accelerated by raising the reaction temperature.

The reaction product of the formula (V) may be isolated and purified by distillation. Examples of the esters of the formula (V) prepared by this reaction are methyl 3-acethylthio-2-methylpropionate, methyl 3-benzoylthio-2-methylpropionate and methyl 3-phenylacetylthio-2-methylpropionate.

The esters of the formula (V) are then asymmetrically hydrolyzed by use of a biochemical process until the optically active carboxylic acids of the formula (VI) are obtained. The biochemical and asymmetrical hydrolysis of the esters is carried out by using enzymes or microorganisms having an ability to asymmetrically hydrolyze the esters. As the microorganisms having an ability to asymmetrically hydrolyze the esters, genuses Torulopsis such as *Torulopsis gropengiesseri*, Aspergillus such as *Aspergillus sojae* IAM 2703, Bacillus such as *Bacillus subtills var niger* IFO 3108, Candida such as *Candida rugosa* IFO 0750, *Candida parapsilosis* IFO 0708 and *Candida utilis* IFO 0396, Botrytis such as *Botrytis cinerea* IAM 5126, Ophiobolus such as *Ophiobolus miyabeanus* IAM 8053, Chaetomium such as *Chaetomium semispirale* IFO 8363, Cladosporium such as *Cladosporium resinae* f. *avellaneum* HUT 5050, Pseudomonas such as *Pseudomonas ovalis* IAM 1049 and IAM 1158, *Pseudomonas putida* IFO 3738 and IFO 12996 and *Pseudomonas fluorescens* IFO 3081 and IFO 12055, Escherichia such as *Escherichia coli* IFO 13500, Staphylococcus such as *Staphylococcus aureus* IFO 12732, Alcaligenes such as *Alcaligenes faecalis* IFO 13111, Streptomyces such as *Streptomyges griseus* IFO 3355 and *Streptoinyces clavuligerus* IFO 13307, Rhodococcus such as *Rhodococcus erythropolis* IFO 12538, IFO 12539 and IFO 12540, Nocardia such as *Nocardia asteroides* IFO 3384, Mycobacterium such as *Mycobacterium phlei* IFO 13160 and Agrobacterium such as *Agrobacterium radiobacter* IFO 12607can be used. And as enzymes, lipase, esterase, chymotrypsin and pancreatin can be used.

In conducting the hydrolysis of the esters by using microorganisms, the esters may be added to a culture medium at the beginning of or during the culturing. Instead of the above, ester may be added to the culture medium where the microorganisms have already been cultured. Alternatively, microorganism cells proliferated may be collected by, for example, centrifugation from the culture medium, and then added to the reaction medium containing the esters. In this aternative case, as a matter of convenience, cells may be used in the form of dried cells such as lyophilized or spray-dried ones or cells treated with organic solvents such as acetone or toluene. In addition, cells may be used in the form of treated cell materials such as destructed cells, or cell extract. When enzymes are used, the enzymes together with the esters are added to a reaction medium.

As the reaction medium, deionized water or a buffer solution may be used. A preferred concentration of the ester in the reaction medium or in the culture medium is 0.01–50% by weight. The ester may be added in the form of a suspension in water. An organic solvent, such as methanol or acetone, may be added to the reaction medium in order to increase the solubility of the ester. The reaction is usually conducted, for example, under pH 2–11, preferably 5–8 and at a temperature of 5°–50° C., although the pH and the temperature may vary depending upon varieties of the microorganisms and enzymes. The pH of the reaction mixture changes as the reaction proceeds accompanying formation of the carboxylic acids. It is preferred to control the pH of the mixture in order to maintain the same at the optimum level by adding a neutralizing agent thereto.

The isolation of the optically active carboxylic acids (VI) from the reaction mixture and purification thereof can be carried out according to any of the conventional methods, for example, extraction, distillation, column chromatography and the like.

Examples of the optically active carboxylic acids prepared by this reaction are D- or L-isomer of 3-acetylthio-2-methylpropionic acid, 3-benzoylthio-2-methylpropionic acid and 3-phenylacetylthio-2-methylpropionic acid.

The thus-prepared optically active carboxylic acids of the formula (VI) are then allowed to react with the amine compounds of the formula (VII). Although the optically active carboxylic acids of the formula (VI) may be used as they are, i.e., in the form of the free acid, it is preferable to use them in the form of reactive derivatives thereof, for example, acid chloride, acid bromide, acid anhydride, mixed acid anhydride and the like. These reactive derivatives are prepared by allowing the optically active carboxylic acids of the formula (VI) to react with, for example, inorganic acid halides, sulfonic acid halides or alkyl halocarbonates. For this purpose, thionyl chloride, phosphorus oxychloride and the like are used as the inorganic acid halides; mesyl chloride, tosyl chloride and the like as the sulfonic acid halides; and ethyl chlorocarbonate, isobutyl chlorocarbonate and the like as the alkyl halocarbonates.

As the compounds of the formula (VII), there may be exemplified proline, thioproline, their esters such as methyl, ethyl and t-butyl esters, and their amides such as prolinamide and thioprolinamide. These compounds may be in the form of a mixture of their D- and L-isomers, or they may be used in their optically active form.

The reaction of the compounds of the formula (VI) with the compounds of the formula (VII) is preferably conducted in a solvent. As the solvent, for example, any of methylene chloride, chloroform, ether, dioxane, toluene, dimethylformamide and tetrahydrofuran may be used. They may be mixed with water. The reaction is preferably conducted in the presence of inorganic bases such as potassium carbonate, sodium carbonate, potassium hydroxide, sodium hydroxide, sodium hydrogencarbonate and the like, or organic bases such as trimethylamine, N,N-dimethylaniline, N,N-dimethylbenzylamine and the like. The reaction temperature is usually −50° C. or higher, preferably in the range of from −20° C. to +50° C.

Typically, N-(3-acetylthio-2-D-methylpropionyl)-L-proline having the formula (II) above, is prepared by allowing thioacetic acid to react with methyl methacrylate, preferably in the presence of polymerization inhibitors such as hydroquinone, to prepare racemic methyl 3-acetylthio-2-D,L-propionate, bringing the propionate obtained after distillation in contact with cells of microorganisms belonging to Pseudomonas, Torulopsis, Agrobacterium or Rhodococcus or disrupted cells thereof in order to effect biochemical and asymmetric hydrolysis, extracting from the hydrolysis product 3-acetylthio-2-D-methylpropionic acid having the formula

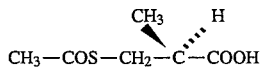

and allowing the acid extracted or reactive derivatives thereof such as acid chloride or acid bromide to react with L-proline.

The microorganisms are, for example, *Torulopsis gropengieseri* IFO 0659, Pseudomonas such as *Pseudomonas ovalis IAM* 1049, *Pseudomonas putida* IFO 3738 and *Pseudomonas fluorescens* IFO 3081, *Rhodococcus erythropolis* IFO 12538 and *Agrobacterium radiobacter* IFO 12607.

The following compounds are examples of the optically active carboxylic acid amides prepared as above, in addition to the N-(3-acetylthio-2-D-methylpropionyl)-L-proline:

N-(3-acetylthio-2D-methylpropionyl)-D-proline, N-(3-acetylthio-2-D-methylpropionyl)-DL-proline, N-(3-acetylthio-2-D-methylpropionyl)-L-thioproline, N-(3-acetylthio-2-D-methylpropionyl)-D-thioproline, N-(3-acetylthio-2-D-methylpropionyl)-DL-thioproline, N-(3-acetylthio-2-D-methylpropionyl)-L-prolinamide, N-(3-acetylthio-2-D-methylpropionyl)-L-thioprolinamide, t-Butyl ester of N-(3-acetylthio-2-D-methylpropionyl)-L-proline, N-(3-benzoylthio-2-D-methylpropionyl)-L-Proline, N-(3-benzoylthio-2-D-methylpropionyl)-DL-proline, N-(3-benzoylthio-2-D-methylpropionyl)-L-thioproline, N-(3-benzoylthio-2-D-methylpropionyl)-DL-thioproline, N-(3-benzoylthio-2-D-methylpropionyl)-L-prolinamide, N-(3-benzoylthio-2-D-methylpropionyl)-L-thioprolinamide, Methyl ester of N-(3-benzoylthio-2-D-methylpropionyl)-L-proline, Methyl ester of N-(3-benzoylthio-2-D-methylpropionyl)-L-thioproline, N-(3-phenylacetylthio-2-D-methylpropionyl)-L-proline, N-(3-acetylthio-2-L-methy propionyl)-DL-proline, N-(3-benzoylthio-2-L-methylpropionyl)-DL-proline, and N-(3phenylacetylthio-2 -L-methylpropionyl)-DL-proline.

According to the present invention, the intermediate optically active carboxylic acid (VI) is easily obtained, and the optically active carboxylic acid amide of the formula (II) is commercially prepared therefrom with great advantages.

The following examples are given to illustrate the present invention more precisely, but it is not intended to limit the present invention thereto.

EXAMPLE 1

(A) Synthesis of methyl 3-acetylthio-2-DL-methylpropionate:

Methyl methacrylate (100 g) containing hydroquinone (200 ppm) were added dropwise to thioacetic acid (123 g) for about 2 hours, while the thioacetic acid was warmed to 50° C. and stirred. Thereafter, the temperature of the mixture was raised to 90° C. and the mixture was allowed to react for about 4 hours. After the reaction was over, the reaction mixture was distilled under reduced pressure and a fraction boilling at 119°–128° C. at 3–4 mmHg was collected and cooled to give methyl 3-acetylthio-2-DL-methylpropionate (152 g).

(B) Synthesis of 3-acetylthio-2-D-methylpropionic acid:

Cells of *Pseudomonas fluorescens* IFO 12055 were collected by centrifugation after the proliferation in a liquid medium (pH 7) containing meat extract (1.0% by weight), peptone (1.0% by weight) and sodium chloride (0.5% by weight). After the cells (10.1 g in terms of dried cell body weight) were suspended in phosphoric acid buffer solution (M/2, 1.5 l, pH 7.0), methyl 3-acetylthio-2-DL-methylpropionate (75 ml) was added to the suspension and allowed to react at 30° C. for 48 hours. After the reaction was over, the cells were removed from the reaction mixture by centrifugation, and the unaltered ester was removed by extraction with an equal volume of ethyl acetate.

After the pH of the resulting aqueous layer was controlled to 2 by addition of sulfuric acid, 3-acetylthio-2-D-methylpropionic acid (30.2 g) was obtained by extraction with an equal volume of ethyl acetate. The specific rotation of the product $[\alpha]_D^{25}$ was −53.8° (C=1.1, CHCl$_3$).

(C) Synthesis of N-(3-acetylthio-2-D-methylpropionyl)-L-proline:

In a flask, 3-acetylthio-2-D-methylpropionic acid (30 g), dimethylformamide (0.5 ml) and thionyl chloride (26 g) were placed, and the mixture was allowed to react at 30° C. overnight. After the reaction was over, the reaction mixture was distilled under reduced pressure and a fraction boiling at 79° C.–85° C. at 2–3 mmHg was collected and cooled to give 3-acetylthio-2-D-methylpropionyl chloride (29.4 g). To L-proline (6.4 g) slurried in N,N-dimethylbenzylamine (20 ml) was added dropwise a solution of the thus-prepared chloride (10 g) in methylene chloride (100 ml), while keeping the reaction temperature at 0° C. After the addition was completed, the mixture was allowed to react at 0° C. for about 1 hour. After the reaction was over, ice water (100 ml) and concentrated hydrochloric acid (10 ml) were added to the reaction mixture and the methylene chloride layer and the aqueous layer were separated with a separatory funnel. The aqueous layer was extracted twice with 100 ml of methylene chloride. The methylene chloride layers were combined with the one previously obtained and washed with 5% hydrochloric acid (100 ml) and twice with ice water (100 ml), and dried over anhydrous sodium sulfate overnight.

Thereafter, methylene chloride was distilled away, leaving N-(3-acetylthio-2-D-methylpropionyl)-L-proline (129 g) as a viscous transparent oily substance. The specific rotation of this oily substance $[\alpha]_D^{29.5}$ was −139° (C=2.1, 99% ethanol). By treating the oily substance with a mixed solvent of n-hexane and ethyl acetate, colorless crystals with a specific rotation $[\alpha]_D^{25°}$ of −161° (C=1.5, 99% ethanol) were obtained. N-(3-acetylthio-2-D-methylpropionyl)-L-proline was identified by N. M. R.

EXAMPLE 2

In the same manner as in example 1(B), cells were prepared by culturing the strains listed in Table 1 in place of the *Pseudomonas fluorescens* IFO 12055.

Methyl 3-acetylthio-2-DL-methylpropionate was assymmetrically hydrolyzed in the same manner as in example 1(C) using cells obtained above. Specific rotations and optical purities of 3-acetylthio-2-D-methylpropionic acid obtained are shown in Table 1.

TABLE 1

| Microorganism | Specific rotation $[\alpha]^{25}_D$ (c = 1, CHCl$_3$) degree | Optical purity (%) |
| --- | --- | --- |
| Agrobacterium radiobacter IFO 12607 | −45.1 | 92.8 |
| Pseudomonas ovalis IAM 1049 | −25.8 | 80.0 |
| Pseudomonas putida IFO 3738 | −22.0 | 90.0 |
| Pseudomonas fluorescens IFO 3081 | −45.0 | 97.0 |
| Torulopis gropengiesseri IFO 0659 | −35.0 | 95.4 |
| Rhodococcus erythropolis IFO 12538 | −41.0 | 91.0 |

Comparative example 1

Production of N-(3-acetylthio-2-D-methylpropionyl)-L-proline from 3-acetylthio-2-DL-methylpropionic acid via methyl 3-acetylthio-2-DL-methylpropionate, asymmetric hydrolysis thereof and 3-acetylthio-2-D-methylpropionic acid.

(1) Esterification of 3-acetylthio-2-DL-methylpropionic acid

To 39.4 g (0.243 mol) of racemic 3-acetylthio-2-methylpropionic acid (39.4 g) and methanol (77.8 g, 2.43 mol), in a flask was added strong acidic cation exchange resin PK-216 H model (36 ml, manufactured by Mitsubishi Chemical Industries Ltd.), and the reaction was carried out at 65° C. for 1 hour. The reaction was monitored with the passage of time by gas chromatography to analyze the components of the reaction mixture. The results are shown in Table 2. Methyl β-mercaptoisobutyrate was produced as a by-product. After 1 hour, 78.7% of the charged carboxylic acid was consumed. Methyl 3-acetylthio-2-DL-methylpropionate as the desired ester was produced (selectivity 86.6%) with by-products.

The reaction mixture was distilled. It was difficult to resolve the desired ester and the by-product, because of their close boiling points. So the purification yield remained 61.7%.

TABLE 2

| Variation with time elapsed of the desired product and by-product | | |
| --- | --- | --- |
| Reaction time (min) | Methyl 3-acetylthio-2-DL-methylpropionate (mol) | Methyl mercaptoisobutyrate (mol) |
| 15 | 0.083 | 0.0062 |
| 30 | 0.138 | 0.0124 |
| 60 | 0.1657 | 0.0247 |

(2) Hydrolysis of the methyl 3-acetylthio-2-DL-methylpropionate according to the present invention with use of microorganisms in Umezawa (U.S. Pat. No. 4,415,657)

*Candida rugosa* IFO 0750, *Pichia farinosa* ISO 534 and *Trichosporon brassicae* IFO 1584 each was inoculated in a liquid culture medium (100 ml) in which glucose (1% by weight), yeast extract (0.5% by weight) and malt extract (0.5% by weight) had been dissolved. Shake incubation was effected at 30° C. for 24 hours. The cells were collected from the culture medium by centrifugation, and the cells were added to 100 ml of M/10 phosphate buffer (pH 7) containing methyl 3-acetylthio-2-DL-methylpropionate (2% by weight). The reaction was conducted at 30° C. for 48 hours. The reaction was monitored with time elapsed by gas chromatography to analyze the components of the reaction mixture. As a result, it was found that substantially no hydrolysis occurred and thus these strains do not hydrolyze methyl 3-acetylthio-2-DL-methylpropionate.

Comparative example 2

Production of N-(3-acetylthio-2-D-methylpropionyl)-L-proline from 3-acetylthio-2-DL-methylpropionic acid.

3-Acetylthio-2-DL-methylpropionic acid was allowed to react with L-proline to obtain N-(3-acetylthio-2-DL-methylpropionil)-L-proline. The product was then subjected to optical resolution to obtain N-(3-acetylthio-2-D-methylpropionyl)-L-proline as the desired compound.

(1) Synthesis of 3-acetylthio-2-DL-methylpropionic acid

The procedure was conducted in the same manner as in Example 1(A) of the present invention except that methacrylic acid was used in place of the methyl methacrylate. The reaction mixture was distilled under reduced pressure, and the fractions of 118°–120° C./0.25–0.5 mmHg were collected to give 3-acetylthio-2-DL-methylpropionic acid. Yield: 85.0%.

(2) Synthesis of N-(3-acetylthio-2-DL-methylpropionyl)-L-proline

The procedure was conducted in the same manner as in Example 1(C) in the present invention except that 3-acetylthio-2-DL-methylpropionic acid was used in place of the 3-acetylthio-2-D-methylpropionic acid.

N-(3-acetylthio-2-DL-methylpropionyl)-L-proline was extracted and recovered from the reaction solution. Yields: 76.0% and 86.0% on the basis of 3-acetylthio-2-DL-methylpropionic acid and L-proline, respectively.

(3) Optical resolution of N-(3-acetylthio-2-DL-methylpropionyl)-L-proline

To a solution of N-(3-acetylthio-2-DL-methylpropionyl)-L-proline (13.7 g) obtained in 2) above in acetonitrile (80 ml) was added dicyclohexylamide (9 ml). After crystals separated were filtered, the crystals were suspended in acetonitrile (200 ml) at 50° C. The suspension was cooled to 5° C. and crystals were recovered by filtration and recrystallized in isopropanol, until dicyclohexylamine salt of N-(3-acetylthio-2-DL-methylpropionyl)-L-proline (6.84 g) was obtained. The amine salt was suspended in ethyl acetate containing potassium bisulfate (5%) and the ethyl acetate layer was recovered. The layer was concentrated and then recrystallized in ethyl acetate until N-(3-acetylthio-2-D-methylpropionyl)-L-proline (2.85 g) was obtained. Yield: 20.8%.

Yields are shown in Table 3 wherein methacrylic acid and methyl methacrylate are used as the starting materials, respectively.

TABLE 3

|  | Example 1 Yield (%) |  | | Comparative example 2 Yield (%) | |
| --- | --- | --- | --- | --- | --- |
| step(A) | 86.3** | — | step(1) | 85.0* | — |
| step(B) | 39.8** | — | step(2) | 76.0* | 86.0*** |
| step(C) | 79.1** | 89.5*** | step(3) | 20.8* | 20.8*** |
| through steps A–C | 27.2** | 89.5*** |  | 13.4* | 17.9*** |

Note)
*based on methacrylic acid
**based on methyl methacrylate
***based on L-proline

We claim:

1. A process for preparing N-(3-acetylthio-2-D-methylpropionyl)-L-proline having the formula:

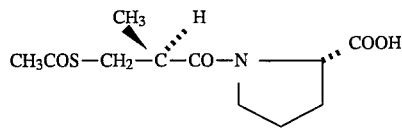

which comprises:

preparing racemic 3-acetylthio-2-DL-methylpropionate by reacting methyl methacrylate with thioacetic acid;

effecting asymmetric hydrolysis of racemic methyl 3-acetylthio-2-DL-methylpropionate by contacting said racemic methyl-3-acetylthio-2-DL-methylpropionate with cells of a microorganism selected from the group consisting of *Pseudomonas ovalis* IAM 1049, *Pseudomonas putida* IFO 3738, *Pseudomonas fluorescens* IFO 3081, *Agrobacterium radiobactor* IFO 12607, *Torulopis gropengienseri* IFO 0659, *Rhodococcus erythropolis* IFO 12538 and disrupted cells thereof;

extracting 3-acetylthio-2-D-methylpropionic acid having the formula:

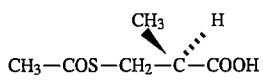

from the hydrolysis medium, optionally halogenating the 3-acetylthio-2-D-methyl-propionic acid;

reacting the extracted 3-acetylthio-2-D-methylpropionic acid or 3-acetylthio-2-D-methylpropanoyl halide with L-proline; and recovering the N-(3-acetylthio-2-D-methylpropionyl)-L-proline product produced from the reaction medium.

2. A process according to claim 1, wherein the asymmetric hydrolysis is carried out in an aqueous solvent wherein the concentration of the racemic propionate is 0.01–50% by weight and reaction temperature is 5°–50° C.

* * * * *